United States Patent
Sumaru et al.

(10) Patent No.: US 9,434,936 B2
(45) Date of Patent: Sep. 6, 2016

(54) METHOD FOR REMOVING CELLS

(75) Inventors: Kimio Sumaru, Tsukuba (JP);
Toshiyuki Takagi, Tsukuba (JP);
Kyoko Kikuchi, Tsukuba (JP); Taku Sato, Tsukuba (JP); Manae Yamaguchi, Tsukuba (JP); Toshiyuki Kanamori, Tsukuba (JP)

(73) Assignee: NATIONAL INSTITUTE OF ADVANCED INDUSTRIAL SCIENCE AND TECHNOLOGY (JP)

( * ) Notice: Subject to any disclaimer, the term of this patent is extended or adjusted under 35 U.S.C. 154(b) by 81 days.

(21) Appl. No.: 13/638,795

(22) PCT Filed: Mar. 28, 2011

(86) PCT No.: PCT/JP2011/057674
§ 371 (c)(1),
(2), (4) Date: Oct. 1, 2012

(87) PCT Pub. No.: WO2011/125615
PCT Pub. Date: Oct. 13, 2011

(65) Prior Publication Data
US 2013/0023025 A1    Jan. 24, 2013

(30) Foreign Application Priority Data
Apr. 2, 2010   (JP) ................. 2010-086132

(51) Int. Cl.
| | | |
|---|---|---|
| *C12N 13/00* | (2006.01) | |
| *C12M 1/00* | (2006.01) | |
| *C12M 1/12* | (2006.01) | |
| *C12M 1/26* | (2006.01) | |
| *C12N 1/02* | (2006.01) | |

(52) U.S. Cl.
CPC .............. *C12N 13/00* (2013.01); *C12M 23/20* (2013.01); *C12M 25/06* (2013.01); *C12M 33/00* (2013.01); *C12M 47/04* (2013.01); *C12N 1/02* (2013.01)

(58) Field of Classification Search
CPC ........ C12N 13/00; C12N 1/02; C12M 23/20; C12M 25/06; C12M 33/00; C12M 47/04
See application file for complete search history.

(56) References Cited

U.S. PATENT DOCUMENTS

| | | | | |
|---|---|---|---|---|
| 4,629,687 A | * | 12/1986 | Schindler et al. | ................. 435/4 |
| 5,906,934 A | * | 5/1999 | Grande et al. | ................. 435/325 |
| 8,119,392 B2 | * | 2/2012 | Gonsalves | ............ G03F 7/0392 |
| | | | | 435/283.1 |
| 2010/0055759 A1 | * | 3/2010 | Blau et al. | ................. 435/173.9 |

FOREIGN PATENT DOCUMENTS

| | | | |
|---|---|---|---|
| EP | 1835344 A1 | * | 9/2007 |
| JP | 08-160607 | | 6/1996 |
| JP | 11-349643 | | 12/1999 |
| JP | 2003-339373 | | 12/2003 |
| JP | 2006-008975 | | 1/2006 |
| JP | 2006008975 A | * | 1/2006 |
| JP | WO 2006/088154 | | 8/2006 |
| JP | 2007-043055 | | 2/2007 |
| JP | 2007-065612 | | 3/2007 |
| JP | 2007146012 A | * | 6/2007 |
| JP | 2007-244378 | | 9/2007 |

OTHER PUBLICATIONS

Wang et al., Langmuir, vol. 22, p. 2719-2725, 2006.*
To'a Salazar et al., Analytical Chemistry, vol. 79, p. 682-687, 2007.*
Rezvin et al., Lab on a Chip, vol. 5, p. 30-37, 2005.*
Takada et al. (JP2007146012A; machine translation).*
A del Campo et al. (Journal of Micromechanics and Microengineering, vol. 17, p. R81-R95, 2007).*
International Search Report and Written Opinion mailed Jun. 28, 2011 in corresponding PCT International Application No. PCT/JP2011/057674.
Kimio Sumaru et al., "On-Demand Manipulation of Adherently Cultured Cells on Thin Layers of Photo-Responsive Polymer Materials," Membrane Symposium, No. 22, pp. 121-124, Oct. 25, 2010.
Yuli Wang et al., "Simple Photografting Method to Chemically Modify and Micropattern the Surface of SU-8 Photoresist," Langmuir, vol. 22(6), pp. 2719-2725, Mar. 14, 2006.
Japanese Office Action dated Nov. 25, 2014 (6 pages).

* cited by examiner

*Primary Examiner* — Susan Hanley
(74) *Attorney, Agent, or Firm* — Ostrolenk Faber LLP

(57) ABSTRACT

A method for separating cells which includes: adhering cells to the surface of a cell culture substrate containing a photo-acid generator that generates an acidic substance upon irradiation with active energy rays, and irradiating only a partial region of the cell culture substrate with the active energy rays to selectively remove the cells within the partial region, thereby separating the cells within the partial region and cells in other regions.

12 Claims, 8 Drawing Sheets

R1

R2

METHOD FOR REMOVING CELLS

CROSS-REFERENCE TO RELATED APPLICATIONS

The present application is a 35 U.S.C. §§371 national phase conversion of PCT/JP2011/057674, filed Mar. 28, 2011, which claims priority of Japanese Patent Application No. 2010-086132, filed Apr. 2, 2010, the contents of which are incorporated herein by reference. The PCT International Application was published in the Japanese language.

TECHNICAL FIELD

The present invention relates to a method for separating cells such as animal cells, a cell culture substrate used in the method, and a cell separation device.

BACKGROUND ART

Examples of cell separation techniques include flow cytometry (FACS: fluorescence-activated cell sorting) and magnetic-activated cell sorting systems (MACS).

These methods are effective in separating and collecting floating cells such as leukocytes and lymphocytes, but when applied to the separation and collection of anchorage-dependent cells, the anchorage-dependent cells that have adhered to the substrate must first be converted to a floating state, by an enzyme treatment using trypsin or the like, or by physical detachment of the cells using an ultrasonic nozzle.

Accordingly, in the techniques described above, the cell adhesion factor or the extracellular matrix may be damaged by the enzyme treatment, or the cell may be damaged by the ultrasound.

An example of a technique that can prevent cell damage is a separation technique that uses a culture substrate containing a temperature-responsive polymeric compound.

In this technique, the adhesiveness of the culture substrate can be increased or decreased by altering the temperature, and therefore cells can be detached and collected without destroying cell adhesion materials and membrane proteins, and with the organ-specific functions of the cell maintained (see Patent Document 1 and Non-Patent Document 1).

DOCUMENTS OF RELATED ART

Patent Document

[Patent Document 1]
Japanese Unexamined Patent Application, First Publication No. Hei 11-349643

Non-Patent Document

[Non-Patent Document 1]
A. Kikuchi, M. Okuhara, F. Karikusa, Y. Sakurai and T. Okano, J. Biomater. Sci., Polym. Edn., 9, 1331 (1998).

DISCLOSURE OF INVENTION

Problems to be Solved by the Invention

However, in a method that uses a temperature-responsive material, using temperature variation to set localized conditions on the culture substrate in order to control the adhesiveness is problematic, and separating and collecting only specific cells from among a plurality of cells has proven difficult.

The present invention has been developed in light of these circumstances, and has an object of providing a method for separating cells, a cell culture substrate and a cell separation device which, when separating specific cells from a plurality of cells on the culture substrate, are able to reliably separate the target cell without causing any damage to the cell.

Means to Solve the Problems

As a result of intensive investigation aimed at achieving the above object, the inventors of the present invention discovered that by using a photo-acid generator that generates an acid upon photoirradiation within the culture substrate, the target cells could be separated without causing any damage to the cells, and they were therefore able to complete the present invention.

The present invention includes the aspects described below.

Namely, a first aspect of the present invention provides a method for separating cells that includes adhering cells to the surface of a cell culture substrate containing a photo-acid generator that generates an acidic substance upon irradiation with the active energy rays, and irradiating only a partial region of the cell culture substrate with active energy rays to selectively remove the cells within the partial region, thereby separating the cells within the partial region and the cells in other regions.

A second aspect of the present invention is the method for separating cells according to the first aspect, wherein when removing the cells from the partial region, the cells within the partial region are removed by killing the cells by irradiation with the active energy rays.

A third aspect of the present invention is the method for separating cells according to the first aspect, wherein when removing the cells from the partial region, the cells within the partial region are removed by detaching the cells from the cell culture substrate by irradiation with the active energy rays.

A fourth aspect of the present invention is the method for separating cells according to the third aspect, wherein the cell culture substrate contains a polyvinylpyridine-based resin.

A fifth aspect of the present invention relates to the method for separating cells according to any one of the first to fourth aspects, wherein a layer containing an adhesion inhibitor is formed on only a partial region of the surface of the cell culture substrate, and the cell culture substrate, which has the cells adhered thereto in the region in which the layer containing an adhesion inhibitor is not formed, is irradiated with the active energy rays.

A sixth aspect of the present invention relates to the method for separating cells according to the any one of the first to fifth aspects, wherein prior to irradiation with the active energy rays, a portion of the cells are labeled, and the region to be irradiated with the active energy rays is determined on the basis of positioning information for the labeled cells.

A seventh aspect of the present invention is a cell culture substrate containing a photo-acid generator that generates an acidic substance upon irradiation with active energy rays.

An eighth aspect of the present invention is the cell culture substrate according to the seventh aspect, wherein a layer containing an adhesion inhibitor is formed on only a partial region of the surface of the cell culture substrate.

A ninth aspect of the present invention is a cell separation device which includes a cell culture substrate containing a photo-acid generator that generates an acidic substance upon irradiation with active energy rays, and an irradiation unit that irradiates the active energy rays onto the surface of the cell culture substrate, wherein the irradiation unit has an active energy ray source and an irradiation region adjustment device that causes the active energy rays from the active energy ray source to be irradiated onto only an arbitrary partial region of the surface of the cell culture substrate.

Effects of the Invention

According to the present invention, because the active energy rays are irradiated onto only a partial region of the cell culture substrate, the acidic substance acts upon only the cells within that region.

Accordingly, the target cells can be separated with good precision, without adversely affecting these target cells.

The present invention is useful in the fields of cellular engineering, regenerative medicine, bio-related industry and tissue engineering.

EMBODIMENTS OF THE INVENTION

Figure 1:
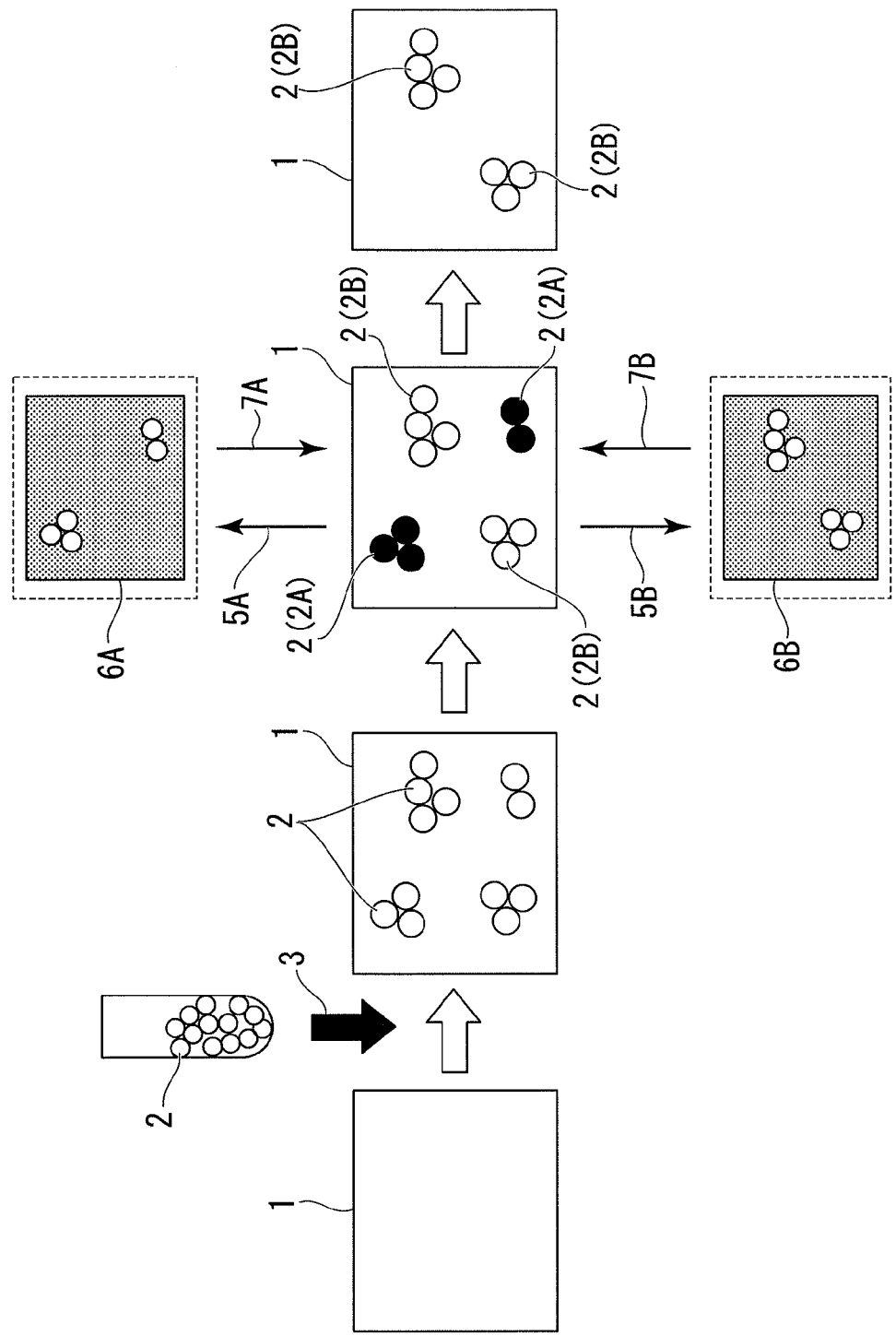
FIG. 1 is a process diagram illustrating one embodiment of a method for separating cells according to the present invention.

The photo-acid generator used in the present invention is a photo-acid generator that is capable of generating an acidic substance upon irradiation with active energy rays such as ultraviolet rays, visible light rays, infrared rays, X-rays, α-rays, β-rays or γ-rays.

For example, a photo-acid generator having a structure formed from a chromophore that absorbs light, and an acid precursor that forms an acidic substance following decomposition can be used as the photo-acid generator.

The pKa of the acidic substance generated by decomposition is typically not more than 3, and preferably 1 or less.

Examples of the photo-acid generator include sulfonic acid derivatives, carboxylate esters, and onium salts.

Examples of the sulfonic acid derivatives include naphthaleneimide-based sulfonic acid derivatives and thioxanthone-based sulfonic acid derivatives.

For example, 1,8 naphthalimide sulfonate can be used as a naphthaleneimide-based sulfonic acid derivative. Further, sulfonic acid 1,3,6-trioxo-3,6-dihydro-1H-11-thia-azacyclopenta[a]anthracen-2-yl ester can be used as a thioxanthone-based sulfonic acid derivative.

Besides these compounds, disulfones, disulfonyldiazomethanes, disulfonylmethanes, sulfonylbenzoylmethanes, imidosulfonates and benzoin sulfonates can also be used as the sulfonic acid derivative.

Examples of the carboxylate esters include 1,8-naphthalenedicarboxylic acid imidomethylsulfonate and 1,8-naphthalenedicarboxylic acid imidotosylsulfonate.

Examples of salts that can be used as the onium salt include sulfonium salts and iodonium salts having an anion such as tetrafluoroborate ($BF_4^-$), hexafluorophosphate ($PF_6^-$) or hexafluoroantimonate ($SbF_6^-$).

Specific examples of the photo-acid generator include compounds (1) to (3d) shown below.

[Chemical Formula 1]

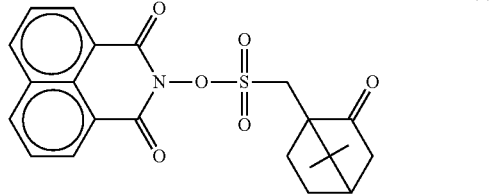

(1)

The compound represented by formula (1) above (hereafter referred to as "compound (1)") is a naphthaleneimide-based sulfonic acid derivative (1,8 naphthalimide camphorsulfonate), and has a chromophore containing a naphthalene backbone (naphthalimide) and an acid precursor that is a sulfonate.

Upon irradiation with active energy rays such as ultraviolet rays having a wavelength of 330 to 380 nm, the compound (1) decomposes in the manner shown below, generating a sulfonic acid as an acidic substance.

[Chemical Formula 2]

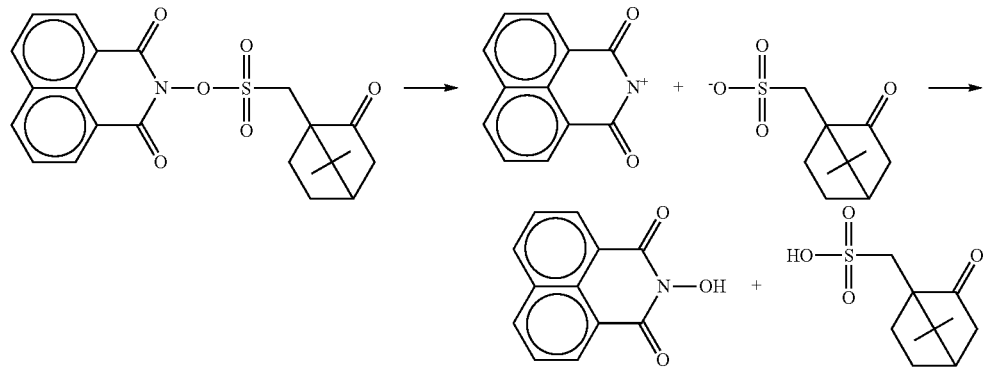

[Chemical Formula 3]

(2)

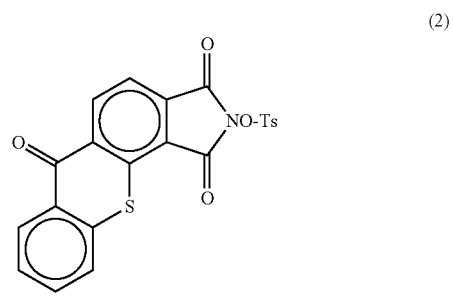

The compound represented by formula (2) above (hereafter referred to as "compound (2)") is a thioxanthone-based sulfonic acid derivative (p-toluenesulfonic acid 1,3,6-trioxo-3,6-dihydro-1H-11-thia-azacyclopenta[a]anthracen-2-yl ester), and has a chromophore containing a thioxanthone backbone and an acid precursor that is a sulfonate. Ts represents a tosyl group.

Upon irradiation with active energy rays such as visible light (blue light) having a wavelength of 400 to 460 nm, the compound (2) decomposes in the manner shown below, generating a sulfonic acid as an acidic substance.

[Chemical Formula 4]

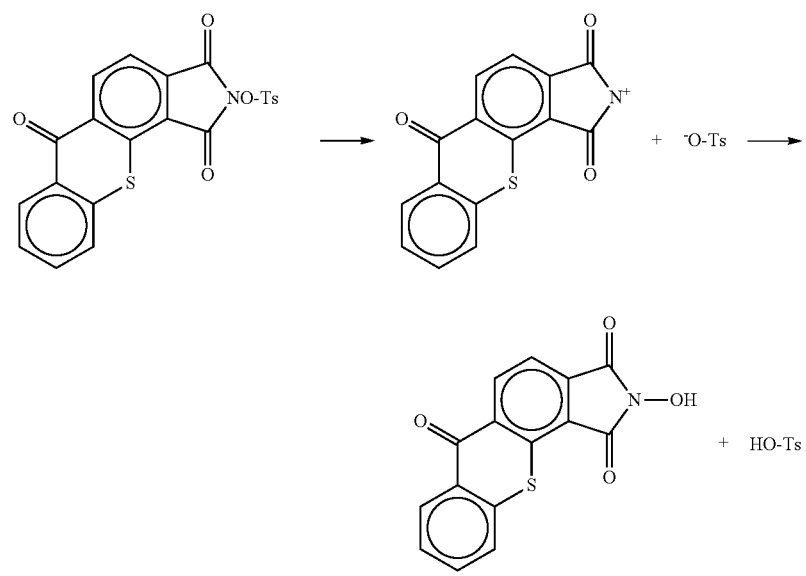

In the case of the compound (2), because the thioxanthone backbone portion formed following decomposition is insoluble in water, it is unlikely to be incorporated within the cells, meaning any effects on the cells can be inhibited.

Further, the compound (2) can generate an acidic substance by irradiation with light from the visible light spectrum. Moreover, because the compound (2) can use light from the visible light spectrum, damage to the cells can be minimized, and because a visible light that exhibits good transmittance through optical lenses is used, the compound (2) also offers the advantage that general-purpose optical lenses can be used.

[Chemical Formula 5]

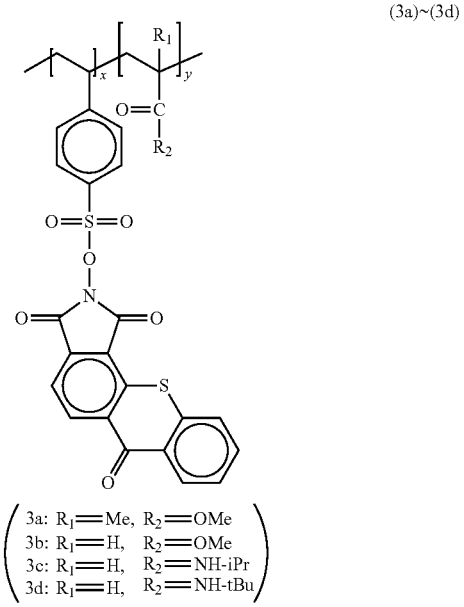

($x$ and $y$ are integers of 1 or greater)

The compounds represented by formulas (3a) to (3d) above (hereafter referred to as "compounds (3a) to (3d)") are thioxanthone-based sulfonic acid derivatives, and each compound has a chromophore containing a thioxanthone backbone and an acid precursor that is a sulfonate. The molar ratio represented by x (namely, the molar ratio of the monomer component (x) containing the thioxanthone backbone relative to the combined total of all the monomer components (x+y)) is typically within a range from 1 to 20 mol %.

Upon irradiation with active energy rays such as ultraviolet rays or visible light (for example, visible light having a wavelength of 400 to 460 nm), the compounds (3a) to (3d) decompose in the manner shown below, generating a polymeric sulfonic acid as an acidic substance.

[Chemical Formula 6]

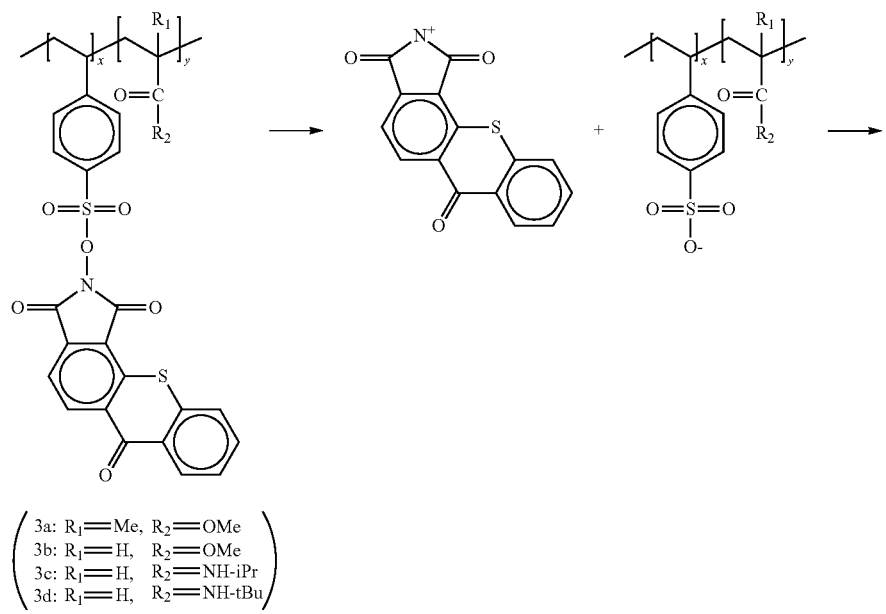

-continued

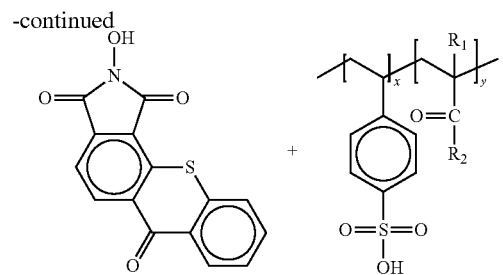

(x and y are integers of 1 or greater)

Because the compounds (3a) to (3d) can use light from the visible light spectrum, damage to the cells can be minimized, and because a visible light that exhibits good transmittance through optical lenses is used, the compounds (3a) to (3d) also offer the advantage that general-purpose optical lenses can be used.

Further, because the generated acidic substance is a polymeric compound, it is less likely to be incorporated within the cells, meaning any effects on the cells can be inhibited. Furthermore, because the thioxanthone backbone portion formed following decomposition is insoluble in water, it is unlikely to be incorporated within the cells, meaning any effects on the cells can be inhibited.

The polymeric acidic substance generated by decomposition of the compound (3b) is soluble in water.

In the present invention, a cell culture substrate containing the photo-acid generator is used to separate a portion of the cells on the surface of the cell culture substrate from the remaining cells.

In other words, in the method for separating cells according to the present invention, two or more cells are adhered to the surface of the cell culture substrate so as to form a single layer, and active energy rays are irradiated onto only a partial region of the cell culture substrate, thus causing the photo-acid generator to act upon only the cells within the partial region. As a result, the cells within the partial region can be selectively removed, thereby enabling the cells within the partial region and the cells in other regions regions to be separated.

Specific examples of the method for separating cells include a method in which the cells within the partial region are killed, and a method in which the cells within the partial region are caused to detach from the cell culture substrate. Each of these methods is described below in detail.

(1) Method for Performing Separation by Killing a Portion of the Cells
(a) Cell Culture Substrate Examples of the materials that can be used for forming the cell culture substrate include plastics, glass, modified glass and metals.

Examples of preferred plastic materials include polystyrene-based resins, acrylic-based resins (such as poly(methyl methacrylate) resin (PMMA)), polyvinylpyridine-based resins (such as poly(4-vinylpyridine) and 4-vinylpyridine-styrene copolymers), silicone-based resins (such as polydimethylsiloxane resin), polyolefin-based resins (such as polyethylene resin, polypropylene resin and polymethylpentene resin), polyester resins (such as polyethylene terephthalate resin (PET)), polycarbonate-based resins and epoxy-based resins.

The photo-acid generator may be incorporated within the material that forms the culture substrate, or a layer containing the photo-acid generator may be formed on (or near) the surface of the substrate.

The aforementioned layer containing the photo-acid generator can be formed, for example, by using a spin-coating method or casting method or the like to apply a raw material liquid containing the photo-acid generator to an aforementioned plastic (such as a polystyrene-based resin or acrylic-based resin), and subsequently curing the applied coating.

The raw material liquid may be prepared, for example, by dissolving the photo-acid generator in a solvent (such as 1,2-dichloroethane or methanol).

In those cases where the photo-acid generator is incorporated within the material that forms the culture substrate, the concentration of the photo-acid generator, reported as the molar concentration of the acid precursor component, is typically within a range from 0.1 to 2 mol/l.

Similarly, in those cases where a layer containing the photo-acid generator is formed on the surface of the culture substrate, the concentration of the photo-acid generator within the layer may be set within the above range.

Figure 3:
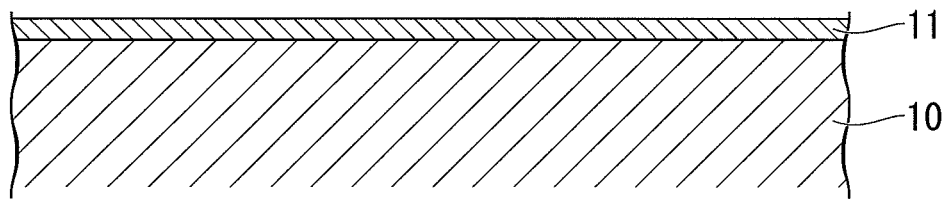
FIG. 3 is a diagram illustrating the structure of one embodiment of a cell culture substrate according to the present invention.

The structure of a cell culture substrate in which a first layer 11 containing a photo-acid generator is formed on the surface of a substrate 10 is illustrated in FIG. 3.

Figure 4:
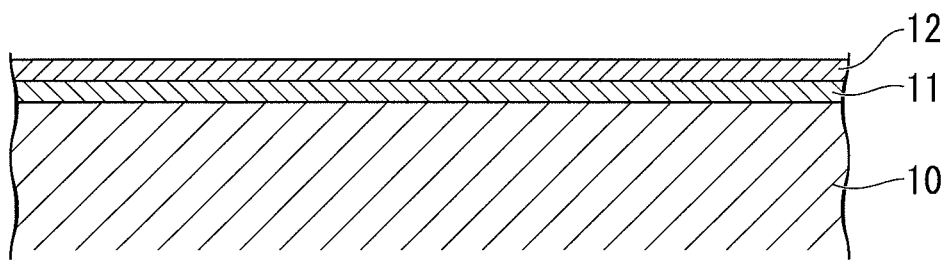
FIG. 4 is a diagram illustrating the structure of another embodiment of the cell culture substrate according to the present invention.

A protective layer composed of gelatin or collagen or the like may also be formed on the surface of the cell culture substrate. For example, as illustrated in FIG. 4, the first layer 11 that acts as the photo-acid generator layer can be formed on the surface of the substrate 10, and a second layer 12 that acts as a protective layer composed of gelatin or collagen or the like can be formed on top of the first layer 11.

A resin containing an azo dye (hereafter also referred to as a "dye polymer"), for example an acrylic-based resin (such as PMMA) containing an azo dye, may also be used as the second layer 12 that acts as a protective layer. By using this type of resin containing an azo dye, superior cell adhesion can be ensured, and any adverse effects of the acidic substance or the active energy rays can be reduced.

A substance that inhibits the adhesion of cells (hereafter also referred to as bonding) (hereafter this substance is also referred to as an adhesion inhibitor), for example one or more polyalkylene glycols selected from the group consisting of polyethylene glycol (PEG), polypropylene glycol, polybutylene glycol, polypentamethylene glycol and polyhexamethylene glycol, or a water-soluble or water-swellable polymer such as a hydroxyl group-containing polyvinyl alcohol, may also be included at the surface of the cell culture substrate.

For example, a layer containing the adhesion inhibitor may be formed on the surface of the substrate. Specifically, such a layer can be formed by applying a raw material liquid containing the adhesion inhibitor to an aforementioned plastic (such as a polystyrene-based resin or acrylic-based resin), and subsequently curing the applied coating.

The layer containing the adhesion inhibitor may be formed by forming a layer containing the photo-acid generator and then a separate layer containing the adhesion inhibitor on the surface of the substrate, or may be formed by forming a single layer containing both the photo-acid generator and the adhesion inhibitor on the substrate surface.

A specific example of the structure of the cell culture substrate is described with reference to FIG. 4. For example, the cell culture substrate may be prepared by forming a first layer 11 that functions as the photo-acid generator layer and a second layer 12 containing an adhesion inhibitor on the surface of a substrate 10.

The concentration of the adhesion inhibitor within the second layer may be set, for example, within a range from 5 to 95% by mass.

The layer containing the adhesion inhibitor (the second layer 12) may be formed on only a partial region of the surface of the substrate (the substrate 10).

Because the adhesion inhibitor can be removed by photoirradiation, if the adhesion inhibitor is removed from a specified region by photoirradiation, then cell adhesion becomes possible within that region.

Hence, in the example illustrated in FIG. 4, the second layer 12 containing the adhesion inhibitor may be formed on only a partial region of the first layer 11. This formation of the second layer 12 in only a partial region can be achieved by a method in which the second layer 12 is initially formed across the entire surface of the first layer 11, and the second layer 12 is then removed from a specified irradiation region by irradiating that region with ultraviolet rays or the like.

Cells can be adhered within the region from which the second layer 12 has been removed. As a result, cells can only be adhered to a specific region.

In other words, by using a photo-acid generator and an adhesion inhibitor in the cell culture substrate, the cell culture substrate exhibits both a photo-writable function (a function that enables the cell adhesion inhibitor to be removed by light irradiation) and a photo-killing function (a function that enables cells to be killed by light).

(b) Cell Separation Device

Figure 2:
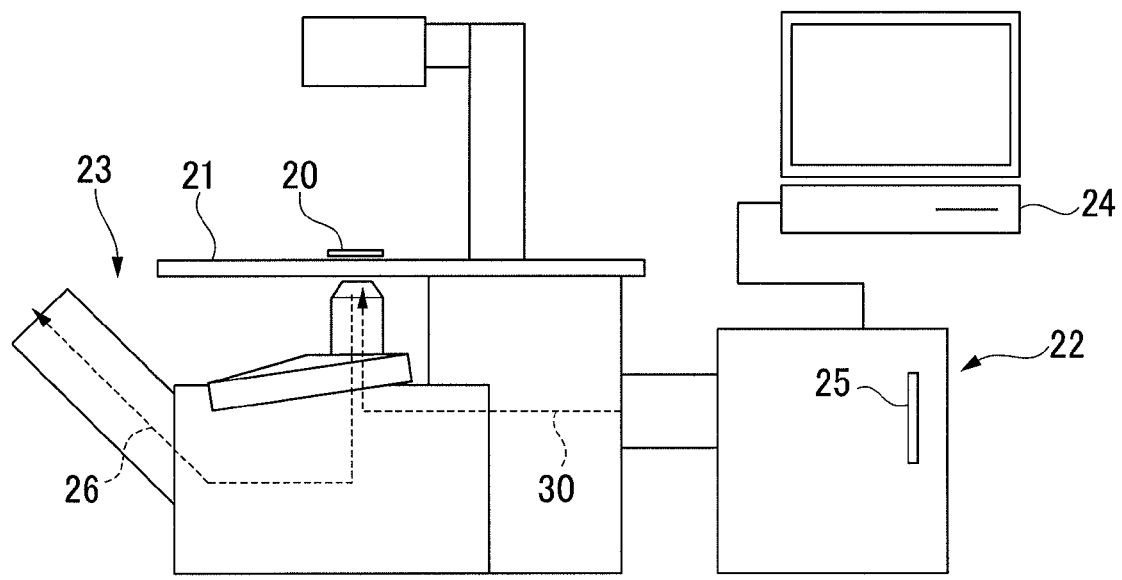
FIG. 2 is a diagram illustrating the structure of one embodiment of a cell separation device according to the present invention.

An example of a cell separation device that can be used in this separation method is illustrated in FIG. 2. This device includes a support base 21 (support unit) that supports a substrate 20 (the cell culture substrate), an irradiation unit 22 that irradiates a light 30 onto an arbitrary region of the substrate 20, an inverted microscope 23 (observation unit) that enables observation of the substrate 20, and a control unit 24 such as a personal computer.

The irradiation unit 22 includes a light source (active energy ray source (not shown in the drawing) and a DMD 25 (digital micromirror device) (irradiation region adjustment device). The DMD 25 is divided into a plurality of micromirrors. The angles of these micromirrors can each be set independently based on a signal from the control unit 24, and by reflecting the light from the light source, a light beam 30 having a pattern that corresponds with the aforementioned signal can be irradiated onto the substrate 20.

By employing this configuration, the DMD 25 can irradiate the light 30 onto any arbitrary region of the substrate 20. The light 30 can be irradiated onto only a partial region having an arbitrary shape on the surface of substrate 20, or alternatively, the light 30 can be irradiated onto the entire surface of the substrate 20.

A light source that is capable of generating the acidic substance from the photo-acid generator is selected as the light source, and for example, a source that is capable of irradiating active energy rays such as ultraviolet rays, visible light rays or infrared rays or the like (such as an ultraviolet lamp or visible light lamp or the like) can be used.

The inverted microscope 23 is able to observe the cells on the substrate 20 using an observation light 26.

The device used for irradiating the light onto only a partial region of the substrate is not limited to a DMD, and other devices such as a liquid crystal shutter array, a light space modulator or a photomask having a desired shape can also be employed.

(c) Target Cells for Separation

There are no particular limitations on the cells that represent the target of the separation of the present invention, and depending on the purpose of the separation, these target cells may be animal-derived cells (such as human cells), plant-derived cells, or microbe-derived cells or the like.

Specific examples include somatic stem cells and embryonic stem cells such as hematopoietic stem cells, myeloid stem cells, neural stem cells and skin stem cells, as well as induced pluripotent stem cells.

Furthermore, leukocytes such as neutrophils, eosinophils, basophils, monocytes and lymphocytes (such as T cells, NK cells and B cells); hemocytes such as platelets, erythrocytes, vascular endothelial cells, lymphoid stem cells, erythroblasts, myeloblasts, monoblasts, megakaryoblasts and megakaryocytes, endothelial cells, epithelial cells, hepatocytes and pancreatic islet cells, as well as various cell lines established for the purpose of research, may all function as the target cells for the present invention.

(d) Separation Method

The method described here is a method for separating cells that includes adhering cells to the surface of a cell culture substrate containing a photo-acid generator that generates an acidic substance upon irradiation with active energy rays, and irradiating only a partial region of the cell culture substrate with the active energy rays to selectively kill the cells within the partial region, thereby separating the cells within the partial region and the cells in other regions.

One example of the method for separating cells according to the present invention is described below with reference to FIG. 1 and FIG. 2.

A plurality of cells 2 are inoculated (symbol 3 in FIG. 1) onto the surface of a cell culture substrate 1 illustrated in FIG. 1 (the substrate 20 in FIG. 2). The cells 2 adhere to the surface of the substrate 1.

The cells 2 may be adhered across the entire surface of the substrate 1, or may be adhered to only a specified region.

In those cases where a substrate 1 that contains an aforementioned adhesion inhibitor (such as PEG) is used, by irradiating active energy rays onto a specified region of the substrate, the adhesion inhibiting properties are weakened by the acidic substance, enabling cell adhesion to occur within this region. As a result, cells can be adhered only within this specified region.

In the example illustrated in FIG. 1, four cells 2 (cell groups) are formed on the surface of the substrate 1 with a separation therebetween.

The cells are observed using the microscope 23 illustrated in FIG. 2, and among the plurality of cells 2, the positional information of the cells 2A is captured by the control unit 24 (symbol 5A in FIG. 1). Using an irradiation pattern 6A (DMD or the like) based on this information, active energy rays (such as ultraviolet rays) are irradiated onto only a partial region on the surface of the substrate 1 (symbol 7A in FIG. 1). In other words, the active energy rays are irradiated onto only the cells 2A and the region of the substrate 1 in which the cells 2A are adhered.

The wavelength band of the active energy rays may be set in accordance with the type of photo-acid generator being used, and is typically within a range from 200 to 1,000 nm. A wavelength of 300 to 800 nm is preferred, and 350 to 600 nm is particularly desirable.

The irradiation energy of the active energy rays is set within a range that is sufficient to kill the cells 2A without having any adverse effects on the cells 2B, and is typically within a range from 0.1 to 10,000 J/cm$^2$, preferably from 1 to 1,000 J/cm$^2$, and more preferably from 10 to 100 J/cm$^2$.

Examples of the cells 2A include cells which, following a gene transfer operation, failed to undergo the desired gene transfer; cells which, following an induced differentiation of ES cells, failed to undergo differentiation; cells among primary cultured cells collected from a biotissue that are deemed unnecessary; and cells having an abnormal shape.

In contrast, examples of the remaining cells (the cells 2B) include cells that have successfully undergone gene transfer, differentiated ES cells, required cells among collected cells, and cells having a normal shape.

The positional information of the cells 2A can be acquired by using observation with the microscope to specify the cells 2A based on their shape or the like.

Further, the positional information of the cells 2A may also be acquired by labeling the cells 2A using a labeling substance such as a dye, a fluorescent substance or a radioactive substance or the like, and then acquiring the positional information of the cells 2A based on the dye or fluorescence intensity.

The irradiation pattern 6A illustrated in the drawing matches the external shape of the cells 2A, enabling the active energy rays to be irradiated onto only the region in which the cells 2A exist. By irradiating these active energy rays, the photo-acid generator contained in the substrate 1 within the irradiated region generates an acidic substance via the decomposition reaction described above.

Generation of the acidic substance kills the cells 2A. Because the cells 2A are killed, it can be stated that these cells 2A have been selectively removed from among the plurality of cells 2.

This separation method is a method in which, by irradiating the active energy rays onto only a partial region of the cell culture substrate 1, thereby generating an acidic substance from the photo-acid generator and killing the cells 2A within the irradiated region, the cells 2A can be separated from the cells 2B outside the irradiated region.

For example, in those cases where the survival rate of the cells 2A following the irradiation with the active energy rays is 10% or less (or 5% or less), the cells 2A can be adjudged to have been killed.

The survival rate can be calculated, for example, using a staining method that is able to distinguish live cells from dead cells (such as Live/Dead staining or trypan blue staining), by counting the number of live cells before and after the active energy ray irradiation using a microscope or the like. The survival rate can be calculated, for example, by determining the live or dead state of at least 100 cells.

The reason that the cells 2A die is thought to be because the generation of the acidic substance causes a localized change in conditions such as the pH, making the conditions unsuitable for survival of the cells 2.

By removing the cells 2A other than the target cells, the target cells 2B can be separated as live cells. Because the acidic substance is generated in a localized manner within only the region that has been subjected to photoirradiation, the cells 2B outside of this irradiated region suffer no damage, even if located close to the irradiated region.

The killed cells 2A can be removed from the substrate 1 by washing or the like with a culture medium or a buffer solution or the like.

According to this method, because the active energy rays are only irradiated onto a partial region of the cell culture substrate 1, the acidic substance acts upon only the cells 2A within this region.

Accordingly, the target cells 2B can be separated from the cells 2A with good precision, and without causing any adverse effects on the target cells 2B.

Because the acidic substance acts upon only the non-target cells 2A, the target cells 2B are able to maintain their organ-specific functions without any damage to the extra-cellular matrix or the protein membrane. As a result, the method is very useful in the fields of cellular engineering, regenerative medicine, bio-related industry and tissue engineering and the like.

In this method, the non-target cells 2A are killed, and therefore the method offers another advantage in that a highly precise separation can be achieved, with no contamination of the cells 2B with live cells of the cells 2A.

(2) Method for Performing Separation by Detaching a Portion of the Cells

This method can also be performed using the cell separation device illustrated in FIG. 2. In the following description, those sections that are common to the previously described "method for performing separation by killing cells" are labeled using the same symbols, and description of these sections is omitted.

(a) Cell Culture Substrate

Materials having the same composition as that described above for the "method for performing separation by killing cells" can be used as the materials for forming the cell culture substrate.

The photo-acid generator may be incorporated within the material that forms the culture substrate, or a layer containing the photo-acid generator may be formed on (or near) the surface of the substrate.

In those cases where the photo-acid generator is incorporated within the material that forms the culture substrate, the concentration of the photo-acid generator, reported as the molar concentration of the acid precursor component, is typically within a range from 0.1 to 2 mol/l.

Similarly, in those cases where a layer containing the photo-acid generator is formed on the surface of the substrate, the concentration of the photo-acid generator within the layer may be set within the above range.

As illustrated in FIG. 3, the material for the cell culture substrate may have a structure in which a first layer 11 that functions as the photo-acid generator layer is formed on the surface of a substrate 10.

In order to induce efficient detachment of the cells, the material that forms this first layer 11 that functions as the photo-acid generator layer may be a material that changes to become water-soluble or water-swellable as a result of the reaction that generates the acidic substance (such as the compound (3b) in which the x molar ratio is approximately 5%).

Further, as illustrated in FIG. 4, the material for the cell culture substrate may have a structure in which a first layer 11 that functions as the photo-acid generator layer is formed on the surface of a substrate 10, and a second layer 12 (protective layer) composed of gelatin, collagen or a dye polymer or the like is then formed on top of the first layer 11.

As described above for the "method for performing separation by killing cells", an adhesion inhibitor may also be included at the surface of the cell culture substrate.

A substrate containing a polyvinylpyridine-based resin can be used as the cell culture substrate.

Examples of resins that may be used as the polyvinylpyridine-based resin include one or more resins selected from among poly(4-vinylpyridine) and 4-vinylpyridine-styrene copolymers.

When using a polyvinylpyridine-based resin, the polyvinylpyridine-based resin may be included within the materials that form the substrate, or a layer containing the polyvinylpyridine-based resin may be formed on (or near) the surface of the substrate.

It is thought that the polyvinylpyridine-based resin functions as a detachment promoting layer, by undergoing a change in structure upon neutralization by reaction with the acidic substance to a hydrophilic state that promotes the detachment of cells. Accordingly, use of a polyvinylpyridine-based resin means that an adequate detachment effect can be achieved even if the amount of the acidic substance is relatively small, which offers the advantage that damage to cells caused by the acidic substance can be minimized.

The polyvinylpyridine-based resin may be used alone, or may be used as part of a mixed resin with other materials.

Figure 5:
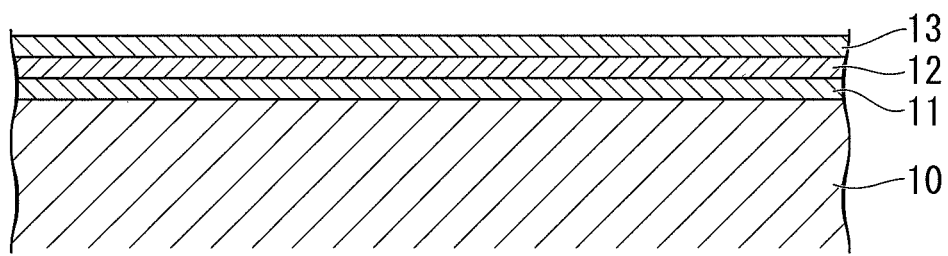
FIG. 5 is a diagram illustrating the structure of yet another embodiment of the cell culture substrate according to the present invention.

An example of the structure of a cell culture substrate that includes a resin layer containing a polyvinylpyridine-based resin (detachment promoting layer) is illustrated in FIG. 5. In this example, a first layer 11 that functions as a photo-acid generator layer is formed on the surface of a substrate 10, a resin layer 12 composed of a polyvinylpyridine-based resin (a detachment promoting layer) is formed on the first layer 11, and a third layer 13 (protective layer) composed of gelatin, collagen or a dye polymer or the like is then formed on top of the resin layer 12.

The polyvinylpyridine-based resin can also be used in the cell culture substrate used in the aforementioned "method for performing separation by killing cells".

(b) Cell Separation Device

The cell separation device described in the aforementioned "method for performing separation by killing cells" (see FIG. 2) can be used.

(c) Target Cells for Separation

The same cells as those described in the aforementioned "method for performing separation by killing cells" may be targeted.

(d) Separation Method

One example of the present method is described below with reference to FIG. 1.

A plurality of cells 2 are inoculated (symbol 3 in FIG. 1) onto the surface of the cell culture substrate 1 illustrated in FIG. 1 (the substrate 20 in FIG. 2). The cells 2 adhere to the surface of the substrate 1. In the present invention, the expression that the "cells adhere" (or bond) means that the position of the cells cannot be moved by certain physical stimuli such as washing with a culture medium or buffer solution or the like. For example, the state wherein the cells do not move when subjected to a washing operation (under a stream of a culture substrate or buffer solution or the like) at a specified shear stress (for example, 0.1 to 10 N/m$^2$) can be defined as an "adhered state". In some cases, cells in the above type of state, or cells that are adhered even more strongly can be described as "bonded" or in a "bonded state", but in the present description, the terms "adhere" and "adhesion" include the meaning of this term "bonded".

The cells are observed using the microscope 23 illustrated in FIG. 2, and among the plurality of cells 2, the positional information of the cells 2A is captured by the control unit 24 (symbol 5A in FIG. 1). Using an irradiation pattern 6A based on this information, active energy rays (such as ultraviolet rays) are irradiated onto only a partial region on the surface of the substrate 1 (symbol 7A in FIG. 1). In other words, the active energy rays are irradiated onto only the cells 2A and the region of the substrate 1 in which the cells 2A are adhered.

The wavelength band of the active energy rays may be set in accordance with the type of photo-acid generator being used, and is typically within a range from 200 to 1,000 nm. A wavelength of 300 to 800 nm is preferred, and 350 to 600 nm is particularly desirable.

The irradiation energy of the active energy rays is set within a range that is sufficient to cause detachment of the cells 2A without having any adverse effects on the cells 2B, and is typically within a range from 0.1 to 10,000 J/cm$^2$, preferably from 1 to 1,000 J/cm$^2$, and more preferably from 10 to 100 J/cm$^2$.

The positional information of the cells 2A can be acquired by using observation with the microscope to specify the cells 2A based on their shape or the like. Further, the positional information of the cells 2A may also be acquired by labeling the cells 2A using a labeling substance such as a dye, a fluorescent substance or a radioactive substance or the like, and then acquiring the positional information of the cells 2A based on the dye or fluorescence intensity.

The irradiation pattern 6A matches the external shape of the cells 2A, enabling the active energy rays to be irradiated onto only the region in which the cells 2A exist. By irradiating these active energy rays, the photo-acid generator contained in the substrate 1 within the irradiated region generates an acidic substance via the decomposition reaction described above.

Generation of the acidic substance causes detachment of the cells 2A from the substrate 1.

In the present invention, "detachment" of the cells means that the cells can be moved from their adhered positions by certain physical stimuli such as washing or the like with a culture medium or buffer solution or the like.

For example, the case where, prior to irradiation with the active energy rays, the cells do not move when subjected to a washing operation at a specified shear stress (for example, 0.1 to 10 N/m$^2$), but performing subsequent irradiation with the active energy rays enables the cells to be moved by a washing operation can be described as "detachment of the cells by irradiation with active energy rays".

Although the mechanism by which the acidic substance causes a change in the adhesion of the cells is unclear, it is thought that a weakening of interactions or bonds between the surface matter of the cells and the substrate 1 under the influence of the acidic substance is a likely cause.

Following detachment, the cells 2A can be selectively removed from the substrate 1 by performing washing or the like of the substrate using a culture medium or a buffer solution or the like.

By removing the non-target cells 2A, the target cells 2B (such as cells that have successfully undergone gene transfer, differentiated ES cells, required cells among collected cells, and cells having a normal shape) can be separated.

According to this method, because the active energy rays are only irradiated onto a partial region of the cell culture substrate 1, the acidic substance acts upon only the cells 2A within this region.

Accordingly, by using this method, the target cells 2B can be separated from the cells 2A with good precision, and without causing any adverse effects on the target cells 2B.

Furthermore, in this method, because the acidic substance acts upon only the cells 2A, the target cells 2B are able to maintain their organ-specific functions without any damage to the extracellular matrix or the protein membrane. As a result, the method is very useful in the fields of cellular engineering, regenerative medicine, bio-related industry and tissue engineering and the like.

In this method, the non-target cells 2A are detached from the substrate, and can therefore by easily removed from the substrate 1 by washing or the like. As a result, the method offers another advantage in that the separation operation is very simple.

In the method described above, the non-target cells 2A are detached and removed, but conversely, the target cells 2B can also be removed and collected.

In other words, as illustrated in FIG. 1, among the plurality of cells 2, the positional information of the cells 2B is captured (symbol 5B in FIG. 1) by the control unit 24 (see FIG. 2), and using an irradiation pattern 6B based on this information, the active energy rays are irradiated onto the cells 2B and the region of the substrate 1 in which the cells 2B are adhered (symbol 7B in FIG. 1). The irradiation pattern 6B matches the external shape of the cells 2B.

Irradiating the active energy rays causes the photo-acid generator to generate the acidic substance, and this generation of the acidic substance causes detachment of the cells 2B from the substrate 1.

Following detachment, by performing washing or the like of the substrate using a culture medium or buffer solution or the like, the cells 2B can be collected within the wash liquid. At this time, the cells 2A are retained on the substrate 1 and do not detach.

As a result, the cells 2B (such as cells that have successfully undergone gene transfer, differentiated ES cells, required cells among collected cells, and cells having a normal shape) can be selectively removed from the substrate 1 and collected, enabling separation of the cells 2B from the cells 2A.

In this method, as was the case described above, the target cells 2B can be separated from the cells 2A with good precision, and without causing any adverse effects on the target cells 2B.

EXAMPLES

The present invention is described below in further detail based on a series of examples, but the present invention is in no way limited by the following examples.

Example 1

A solution containing the compound (1) (NAI-106, manufactured by Midori Kagaku Co., Ltd.) was applied to the surface of a substrate composed of polystyrene and then dried to form a layer containing the compound (1), and a gelatin layer was then formed on top. This yielded a cell culture substrate 1 having a layer containing the compound (1) and a gelatin layer provided on top of the surface of the substrate.

The surface of the substrate 1 was inoculated with MDCK cells across the entire surface of the substrate.

Subsequently, ultraviolet rays (wavelength: 365 nm) were irradiated (irradiation energy: 6 J/cm$^2$) onto only a partial region of the substrate 1 (see FIG. 1), while the substrate 1 was observed using a microscope 23 illustrated in FIG. 2.

The results of performing Live/Dead staining, which fluorescently stains live cells green and dead cells red, confirmed that only the cells within the irradiated region were killed.

Examples 2 to 4

A cell culture substrate 1 having a layer composed of PMMA containing the compound (1) on the surface of the substrate was inoculated with one type of cell selected from among MDCK cells (example 2), Hek293 cells (example 3) and NIH/3T3 cells (example 4), and ultraviolet rays (wavelength: 365 nm) were then irradiated onto only a partial region of the cell culture substrate. The remaining conditions were the same as those described for the example 1.

The results of performing Live/Dead staining confirmed that only the cells within the irradiated region were killed.

Examples 5 and 6

A cell culture substrate 1 having a layer composed of PMMA containing the compound (2) on the surface of the substrate was inoculated with one type of cell selected from among CHO-K1 cells (example 5) and NIH/3T3 cells (example 6), and a visible light (wavelength: 436 nm) was then irradiated onto only a partial region of the cell culture substrate. The remaining conditions were the same as those described for the example 1.

The results of performing Live/Dead staining confirmed that only the cells within the irradiated region were killed.

Examples 7 to 10

A cell culture substrate 1 having a layer containing the compound (3a) (x molar ratio: 1.0 mol %) on the surface of the substrate was inoculated with one type of cell selected from among CHO-K1 cells (example 7), MDCK cells (example 8), Hek293 cells (example 9) and NIH/3T3 cells (example 10), and a visible light (wavelength: 436 nm) was then irradiated onto only a partial region of the cell culture substrate. The remaining conditions were the same as those described for the example 1.

The results of performing Live/Dead staining confirmed that only the cells within the irradiated region were killed.

Figure 6:
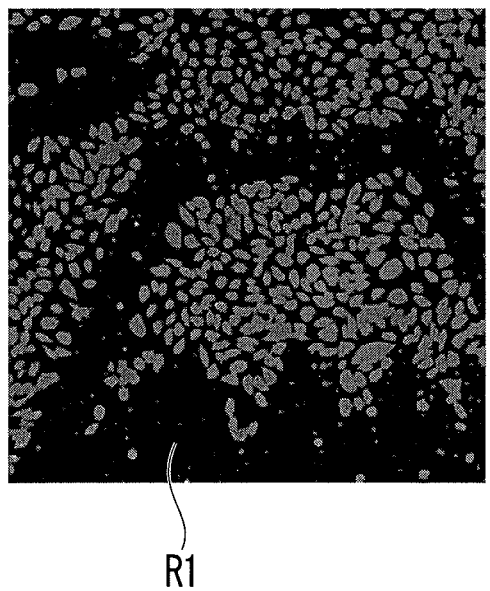
FIG. 6 is a photograph illustrating the state of cells on a cell culture substrate in an example of the present invention.

The state of the cells following Live/Dead staining in the case of the CHO-K1 cells (example 7) is illustrated in FIG. 6. The portion that appears dark indicates the visible light-irradiated region R1, and it was confirmed that the cells in this region R1 were dead.

Figure 7:
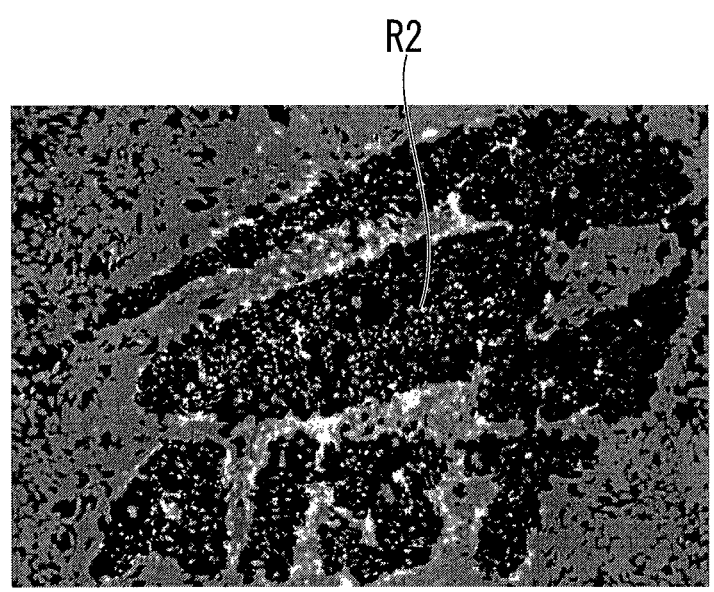
FIG. 7 is a photograph illustrating the state of cells on a cell culture substrate in an example of the present invention.

The state of the cells following Live/Dead staining in the case of the NIH/3T3 cells (example 10) is illustrated in FIG. 7. The portion that appears dark indicates the visible light-irradiated region R2, and it was confirmed that the cells in this region R2 were dead.

Example 11

A cell culture substrate 1 having a layer containing the same compound (1) as that used in the examples 7 to 10 on the surface of the substrate was inoculated with CHO-K1 cells. A portion of the cells 2A were labeled with a staining red fluorescent dye (DiI) regardless of whether the cells were live or dead, and following cell adhesion, the cells were stained with Calcein AM which stains only the live cells green, and it was confirmed that the cells 2A exhibited yellow fluorescence (namely, a combination of red+green fluorescence, whereas in the case of a dead cell, the green fluorescence is lost, resulting in a red color), whereas the remaining cells exhibited green fluorescence. Subsequently, a visible light (wavelength: 436 nm) was irradiated onto only the partial region containing the cells 2A. The remaining conditions were the same as those described for the example 1.

Figure 8A:
FIG. 8A is a photograph illustrating the state of cells on a cell culture substrate prior to irradiation with active energy rays in an example according to the present invention.

The state of the cells on the cell culture substrate prior to irradiation of the visible light is illustrated in FIG. 8A. It was confirmed that the cells 2A could be distinguished from the other cells by the fluorescent labeling, and that all of the cells were alive.

Figure 8B:
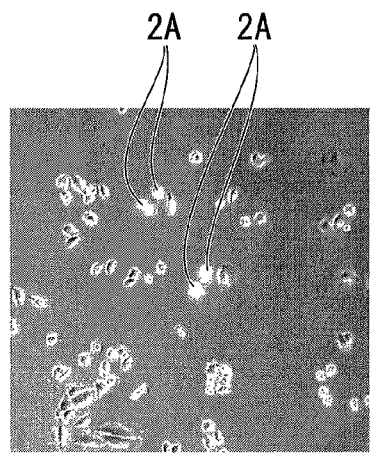
FIG. 8B is a photograph illustrating the state of cells on a cell culture substrate during irradiation with active energy rays in an example of the present invention.

The state during irradiation of the visible light onto only the cells 2A on the cell culture substrate is illustrated in FIG. 8B.

Figure 8C:
FIG. 8C is a photograph illustrating the state of cells on a cell culture substrate following irradiation with active energy rays in an example of the present invention.

The state of the cells on the cell culture substrate following irradiation of the visible light is illustrated in FIG. 8C. The fluorescence confirmed that only the cells 2A had been killed, whereas the other cells remained alive.

Examples 12 and 13

A cell culture substrate 1 having a layer containing the compound (3b) (x molar ratio: 4.3 mol %) on the surface of the substrate was inoculated with one type of cell selected from among CHO-K1 cells (example 12) and NIH/3T3 cells (example 13), and a visible light (wavelength: 436 nm) was then irradiated onto only a partial region of the cell culture substrate. The remaining conditions were the same as those described for the example 1.

The results of performing Live/Dead staining confirmed that only the cells within the irradiated region were killed.

Examples 14 and 15

A cell culture substrate 1 having a layer containing the compound (3d) (x molar ratio: 1.4 mol %) on the surface of the substrate was inoculated with one type of cell selected from among CHO-K 1 cells (example 14) and NIH/3T3 cells (example 15), and a visible light (wavelength: 436 nm) was then irradiated onto only a partial region of the cell culture substrate. The remaining conditions were the same as those described for the example 1.

The results of performing Live/Dead staining confirmed that only the cells within the irradiated region were killed.

Examples 16 and 17

A cell culture substrate 1 having a resin layer composed of poly(4-vinylpyridine) containing the same compound (3d) as that used in the examples 14 and 15 on the surface of the substrate was inoculated with one type of cell selected from among Hek293 cells (example 16) and NIH/3T3 cells (example 17), and ultraviolet rays (wavelength: 365 nm) were then irradiated onto only a partial region of the cell culture substrate. The remaining conditions were the same as those described for the example 1.

The results of performing Live/Dead staining confirmed that only the cells within the irradiated region were killed.

Example 18

A photo-acid generator layer containing the same compound (3a) as that used in the examples 7 to 10 was formed, and a cell adhesion inhibiting layer composed of PEG was then formed on top of the photo-acid generator layer. Subsequently, ultraviolet rays (wavelength: 365 nm) were irradiated onto only a partial region of the resulting cell culture substrate 1, which had been imparted with a photo-writable function and a photo-killing function, thereby removing the cell adhesion inhibiting layer from this region, and the partial region was then inoculated with CHO-K1 cells.

A visible light (wavelength: 436 nm) was then irradiated onto a portion of this region. The remaining conditions were the same as those described for the example 1.

Figure 9A:
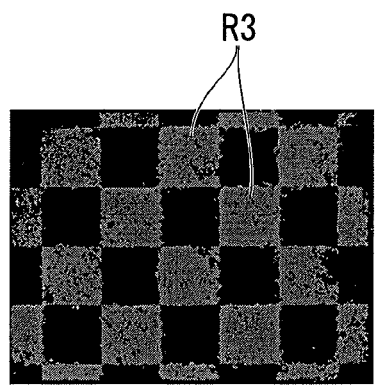
FIG. 9A is a photograph illustrating the state of cells on a cell culture substrate prior to irradiation with active energy rays in an example of the present invention.

The state of the cells on the cell culture substrate prior to the irradiation with visible light is illustrated in FIG. 9A. Irradiation of ultraviolet rays (wavelength: 365 nm) onto the rectangular regions R3 of the cell culture substrate 1 caused removal of the cell adhesion inhibiting layer from these regions, and adhesion of cells was confirmed within these regions R3.

Figure 9B:
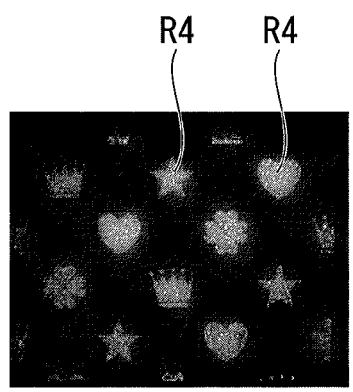
FIG. 9B is a photograph illustrating the state of cells on a cell culture substrate during irradiation with active energy rays in an example of the present invention.

The state during irradiation of the aforementioned visible light (wavelength: 436 nm) onto regions R4, which had predetermined shapes that represented a portion of the regions R3 to which cells had been adhered, is illustrated in FIG. 9B.

Figure 9C:
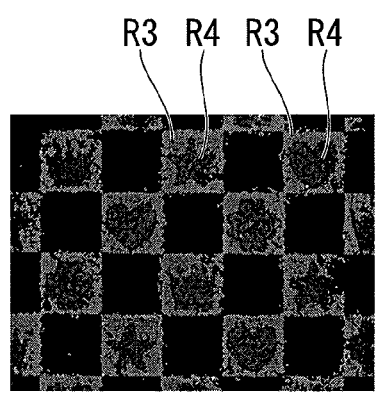
FIG. 9C is a photograph illustrating the state of cells on a cell culture substrate following irradiation with active energy rays in an example of the present invention.

The state following Live/Dead staining of the cells on the cell culture substrate following irradiation of the visible light is illustrated in FIG. 9C. The fluorescence confirmed that the cells within the irradiation regions R4 were dead.

Comparative Example 1

The surface of a substrate composed of polystyrene was inoculated with CHO-K1 cells across the entire surface of the substrate, and the surface of the substrate was then irradiated with ultraviolet rays (wavelength: 365 nm). The irradiation energy was set to 6 J/cm$^2$, 28 J/cm$^2$ or 69 J/cm$^2$.

The cell proliferation properties within the irradiated region were evaluated by comparing the fluorescence intensity upon addition of CyQUAT with the fluorescence intensity observed under reference conditions that involved no irradiation. CyQUAT emits fluorescence with an intensity that is proportional to the number of cells.

The results revealed that under each of the irradiation conditions, cell proliferation was at least 90% of that observed under the non-irradiation reference conditions. These results indicate that the majority of cells were not killed under any of the irradiation conditions.

Further, the adhesion of cells within the irradiated area was evaluated by washing the surface of the substrate with a phosphate buffer solution containing 1 mM of EDTA, and then confirming the amount of remaining cells by visual observation. The cell survival rate following a washing operation sufficient to remove the non-irradiated cells was at least 80% under each of the irradiation conditions.

Comparative Example 2

The surface of a substrate composed of polystyrene was inoculated with NIH/3T3 cells across the entire surface of the substrate, and only a partial region of the surface of the substrate was then irradiated with a visible light (wavelength: 436 nm). The irradiation energy was set to 75 J/cm$^2$, 150 J/cm$^2$ or 300 J/cm$^2$.

Using trypan blue, which has a property of staining only dead cells, staining of the cells within the irradiated region revealed that the cell fatality rate was 1% or less under each of the irradiation conditions, and no significant difference was observed compared with the non-irradiated region. Further, no cell detachment was observed under any of the conditions.

Whereas no cell death occurred in the comparative example 1, in the examples 1 to 4 and 16 to 18, the majority of the cells in the irradiated region were killed, despite using ultraviolet rays having the same wavelength as the comparative example 1 and having a similar or lower irradiation energy, and it is therefore thought that the cell death occurred due to the action of the photo-acid generator.

Similarly, whereas no cell death occurred in the comparative example 2, in the examples 5 to 15, the majority of the cells in the irradiated region were killed, despite using a visible light having the same wavelength as the comparative example 2 and having a lower irradiation energy, and it is therefore thought that the cell death occurred due to the action of the photo-acid generator.

Example 19

A cell culture substrate 1 having a layer containing the compound (1) and a resin layer composed of poly(4-vinylpyridine) formed thereon was inoculated with MDCK cells, and only a partial region of the substrate was then irradiated (irradiation energy: 17 J/cm$^2$) with ultraviolet rays (wavelength: 365 nm). The remaining conditions were the same as those described for the example 1.

The surface of the cell culture substrate 1 was washed with PBS (phosphate buffer solution), and subsequent observation of the surface of the cell culture substrate 1 confirmed that the majority (approximately 90% or more) of the cells in the irradiated region had been detached and removed.

Figure 10A:
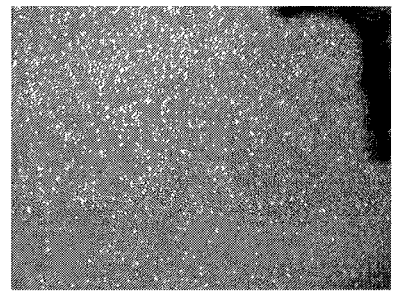
FIG. 10A is a photograph illustrating the state of cells on a cell culture substrate prior to irradiation with active energy rays in an example of the present invention.

The state of the cells on the cell culture substrate prior to the aforementioned irradiation with ultraviolet rays is illustrated in FIG. 10A. It is evident that cells are adhered across substantially the entire surface within the field of view.

Figure 10B:
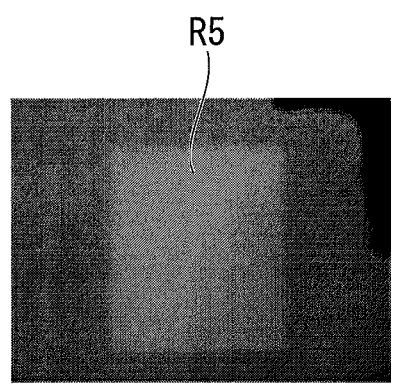
FIG. 10B is a photograph illustrating the state of cells on a cell culture substrate during irradiation with active energy rays in an example of the present invention.

The state during irradiation of ultraviolet rays onto a central rectangular region R5 is illustrated in FIG. 10B.

Figure 10C:
FIG. 10C is a photograph illustrating the state of cells on a cell culture substrate following irradiation with active energy rays in an example of the present invention.

The state of cells on the cell culture substrate following the irradiation with ultraviolet rays is illustrated in FIG. 10C. It was confirmed that a portion of the cells within the irradiated region R5 had detached.

Examples 20 and 21

A cell culture substrate 1 having a layer containing the compound (2), a resin layer composed of poly(4-vinylpyridine) formed thereon, and a gelatin layer formed on top was inoculated with one type of cell selected from among MDCK cells (example 20) and Hek293 cells (example 21), and only a partial region of the substrate was then irradiated with a visible light (wavelength: 436 nm). The remaining conditions were the same as those described for the example 19.

When the surface of the cell culture substrate 1 was washed with PBS (phosphate buffer solution), it was confirmed that the majority of the cells in the irradiated region had been detached and removed.

Example 22

A cell culture substrate 1 having a layer composed of PMMA containing the compound (2), a resin layer composed of poly(4-vinylpyridine) formed thereon, and a gelatin layer formed on top was inoculated with Hek293 cells, and only a partial region of the substrate was then irradiated with a visible light (wavelength: 436 nm). The remaining conditions were the same as those described for the example 19. When the surface of the cell culture substrate 1 was washed with PBS (phosphate buffer solution), it was confirmed that the majority of the cells in the irradiated region had been detached and removed.

Example 23

A cell culture substrate 1 having a layer composed of PMMA containing the compound (2), a resin layer formed thereon, and a gelatin layer formed on top was inoculated with Hek293 cells, and only a partial region of the substrate was then irradiated with a visible light (wavelength: 436 nm). The resin layer employed a mixed resin composed of poly(4-vinylpyridine) and polyvinyl acetate. The remaining conditions were the same as those described for the example 19.

When the surface of the cell culture substrate 1 was washed with PBS (phosphate buffer solution), it was confirmed that the majority of the cells in the irradiated region had been detached and removed.

Example 24

A cell culture substrate 1 having a layer composed of PMMA containing the compound (2) and a resin layer formed thereon was inoculated with Hek293 cells, and only a partial region of the substrate was then irradiated with a visible light (wavelength: 436 nm). The resin layer employed a copolymer of 4-vinylpyridine and styrene. The remaining conditions were the same as those described for the example 19.

When the surface of the cell culture substrate 1 was washed with PBS (phosphate buffer solution), it was confirmed that the majority of the cells in the irradiated region had been detached and removed.

Examples 25 and 26

A cell culture substrate 1 having a layer containing the same compound (3a) as that used in the examples 7 to 10, and a resin layer composed of poly(4-vinylpyridine) formed thereon was inoculated with one type of cell selected from among Hek293 cells (example 25) and MDCK cells (example 26), and only a partial region of the substrate was then irradiated with a visible light (wavelength: 436 nm). The remaining conditions were the same as those described for the example 19.

When the surface of the cell culture substrate 1 was washed with PBS (phosphate buffer solution), it was confirmed that the majority of the cells in the irradiated region had been detached and removed.

Examples 27 and 28

A cell culture substrate 1 having a layer containing the same compound (3a) as that used in the examples 7 to 10, and a resin layer formed thereon was inoculated with one type of cell selected from among Hek293 cells (example 27) and NIH/3T3 cells (example 28), and only a partial region of the substrate was then irradiated with a visible light (wavelength: 436 nm). The resin layer employed a copolymer of 4-vinylpyridine and styrene. The remaining conditions were the same as those described above for the example 19.

When the surface of the cell culture substrate 1 was washed with PBS (phosphate buffer solution), it was confirmed that the majority of the cells in the irradiated region had been detached and removed.

Example 29

A cell culture substrate 1 having a layer containing the compound (3c) (x molar ratio: 1.0 mol %) on the surface of the substrate was inoculated with Hek293 cells, and only a partial region of the substrate was then irradiated with a visible light (wavelength: 436 nm). The remaining conditions were the same as those described for the example 19.

When the surface of the cell culture substrate 1 was washed with PBS (phosphate buffer solution), it was confirmed that the majority of the cells in the irradiated region had been detached and removed.

Example 30

A cell culture substrate 1 having a first resin layer composed of poly(4-vinylpyridine) containing the same compound (3b) as that used in the examples 12 and 13, and a protective layer formed thereon was inoculated with NIH/3T3 cells, and only a partial region of the substrate was then irradiated with a visible light (wavelength: 436 nm).

The protective layer employed a PMMA having an azo dye (Disperse Red 1) as a side chain (manufactured by Aldrich Co., Ltd.). The remaining conditions were the same as those described for the example 19.

When the surface of the cell culture substrate 1 was washed with PBS (phosphate buffer solution), it was confirmed that the majority of the cells in the irradiated region had been detached and removed.

Example 31

A cell culture substrate 1 having a layer containing the same compound (3b) as that used in the examples 12 and 13, and a resin layer composed of a copolymer of 4-vinylpyridine and styrene formed thereon was inoculated with NIH/3T3 cells, and only a partial region of the substrate was then irradiated with a visible light (wavelength: 436 nm). The remaining conditions were the same as those described for the example 19.

When the surface of the cell culture substrate 1 was washed with PBS (phosphate buffer solution), it was confirmed that the majority of the cells in the irradiated region had been detached and removed.

Figure 11A:
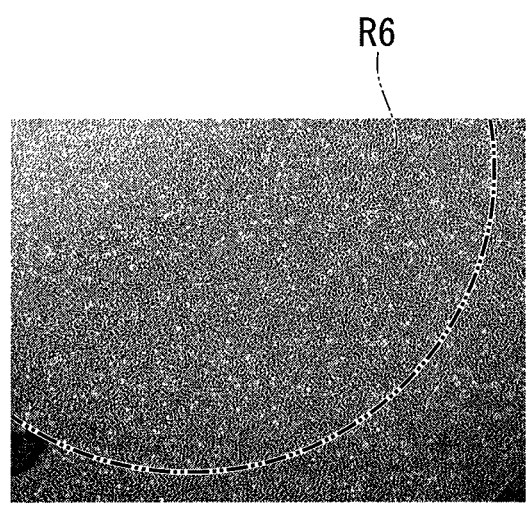
FIG. 11A is a photograph illustrating the state of cells on a cell culture substrate prior to irradiation with ultraviolet rays in an example of the present invention.

The state of the cells on the cell culture substrate prior to the aforementioned irradiation with visible light is illustrated in FIG. 11A. It is evident that cells are adhered across substantially the entire surface within the field of view.

Figure 11B:
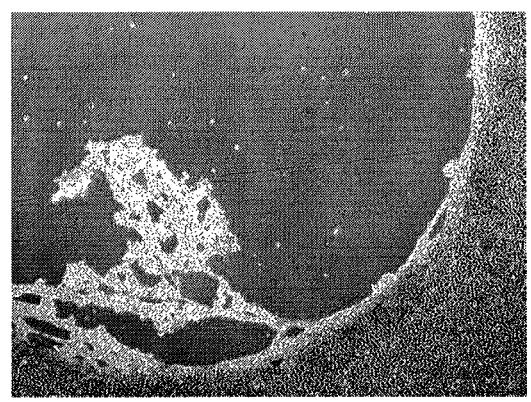
FIG. 11B is a photograph illustrating the state of cells on a cell culture substrate following irradiation with ultraviolet rays in an example of the present invention.

The state of cells on the cell culture substrate following the irradiation with visible light is illustrated in FIG. 11B. It was evident that the majority of the cells in the visible light-irradiated region (the substantially sector-shaped region R6 indicated by the dashed line in FIG. 11A) had been detached and removed.

Trypan blue staining confirmed that 80% or more of the detached and collected cells were still alive.

Comparative Example 3

A protective layer composed of the same PMMA having an azo dye as a side chain used in the example 30 was formed on the surface of a substrate composed of polystyrene, the surface of the substrate was then inoculated with one type of cell selected from among HepG2 cells, Hek293 cells, NIH/3T3 cells and MDCK cells, and only a partial region of the substrate was then irradiated with a visible light (wavelength: 436 nm). The irradiation energy was set to 120 J/cm$^2$ or 240 J/cm$^2$.

The results revealed that under each of the irradiation conditions, no cell detachment was observed. Further, staining of the cells within the irradiated region using trypan blue revealed that the cell fatality rate was 1% or less, and no significant difference was observed compared with the non-irradiated region.

Whereas the cell survival rate following washing of the substrate surface in the aforementioned comparative example 1 was at least 80%, in the example 19, detachment of the cells occurred, despite using ultraviolet rays having the same wavelength as the comparative example 1 and having a lower irradiation energy, and it is therefore thought that the cell detachment occurred due to the action of the photo-acid generator.

Whereas no detachment of the cells was observed in the aforementioned comparative example 2, in the examples 20 to 31, detachment of the cells occurred, despite using visible light having the same wavelength as the comparative example 2 and having a lower irradiation energy, and it is therefore thought that the cell detachment occurred due to the action of the photo-acid generator.

Further, whereas no cell detachment was observed in the comparative example 3, in the example 30, detachment of the cells occurred, despite using visible light having the same wavelength as the comparative example 3 and having a lower irradiation energy. Based on this observation, it can be determined that the cell detachment occurred due to the action of the photo-acid generator.

INDUSTRIAL APPLICABILITY

According to the present invention, because the acidic substance acts upon only specific cells, the target cells can be separated without damaging the cells, and therefore the invention can be used in the fields of cellular engineering, regenerative medicine, bio-related industry and tissue engineering, and is extremely useful industrially.

DESCRIPTION OF THE REFERENCE SIGNS 1, 20: Cell culture substrate
2: Cell
22: Irradiation unit

The invention claimed is:

1. A method for removing target cells from a cell culture substrate, the method comprising:
   providing a cell culture substrate including a substrate and a layer containing a photo-acid generator formed on a surface of the substrate:
   adhering cells to the surface of the layer containing the photo-acid generator which generates an acidic substance upon irradiation with light,
   generating the acidic substance by irradiating only a region of the substrate containing the photo-acid generator layer beneath target cells to be removed, and
   removing the target cells from the region of the irradiated substrate by the action of the acidic substance generated from the irradiated layer containing the photo-acid generator beneath the target cells.

2. The method for removing target cells according to claim 1, wherein the removal is conducted by killing the target cells by the action of the acidic substance generated from the irradiated layer containing the photo-add generator beneath the removal target cells.

3. The method for removing cells according to claim 1, wherein the substrate comprises a polyvinylpyridine-based resin.

4. The method for removing target cells according to claim 1, wherein
a layer containing an adhesion inhibitor is formed on only a partial region of the surface of the layer containing the photo-acid generator, and
the layer containing the photo-acid generator, which has the target cells adhered thereto in a region in which the layer containing an adhesion inhibitor is not formed, is irradiated with light.

5. The method for removing cells according to claim 1, wherein prior to irradiation with the light, a portion of the cells are labeled, and a region to be irradiated with light is determined based on positioning information for the labeled cells.

6. The method for removing cells according to claim 1, wherein
the photo-acid generator is at least one member selected from the group consisting of a naphthaleneimide-based sulfonic acid derivative, a thioxanthone-based sulfonic acid derivative, 1,8-naphthalenedicarboxylic acid imidomethylsulfonate, 1,8-naphthalenedicarboxylic acid imidotosylsulfonate, and sulfonium salts or iodonium salts having an anion which is tetrafluoroborate ($BF_4^-$) or hexafluorophosphate ($PF_6^-$).

7. The method for removing cells according to claim 1, wherein
the photo-acid generator is at least one member selected from the group consisting of a compound represented by formula (1) and a compound represented by formula (2) shown below:

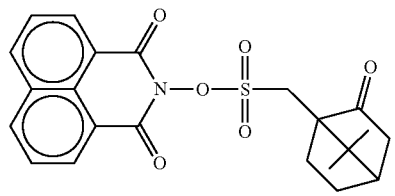
(1)

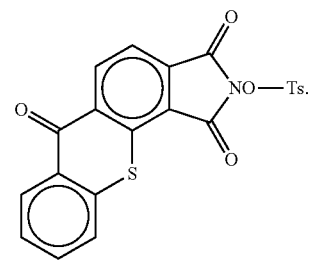
(2)

8. The method for removing cells according to claim 1, wherein
the photo-acid generator includes a compound which generates an acidic substance by irradiation with the light, and
the acidic substance is a polymeric compound.

9. The method for removing cells according to claim 8, wherein the photo-acid generator is at least one member select from the group consisting of a compound represented by formula (3a), a compound represented by formula (3b), a compound represented by formula (3c) and a compound represent by formula (3d):

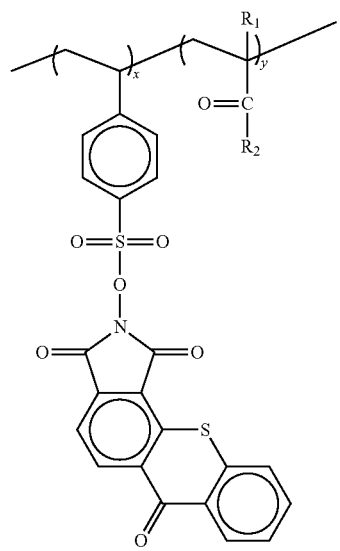

wherein
for the compound represented by formula 3(a): $R_1$ is Me and $R_2$ is OMe;
for the compound represented by 3(b): $R_1$ is H and $R_2$ is OMe;
for the compound represented by 3(c): $R_1$ is H and $R_2$ is NH-iPr; and
for the compound represented by 3(d): $R_1$ is H and $R_2$ is NH-iPr; wherein x and y are integers of 1 or greater.

10. The method for removing cells according to claim 1, wherein the light has a wavelength of 200 to 600 nm.

11. The method for removing cells according to claim 1, wherein a light source of the light is an ultraviolet lamp or a visible light lamp.

12. The method for removing target cells according to claim 1, wherein the step of removing the target cells is by washing the irradiated substrate with a culture medium or a buffer solution thereby detaching the target cells.

* * * * *